United States Patent
Dye et al.

[19]

[11] Patent Number: 6,080,162
[45] Date of Patent: Jun. 27, 2000

[54] MODULAR ORTHOPAEDIC CLAMPING TOOL

[75] Inventors: Justin Dye, Mansfield; George Cipolletti, Duxbury; James Boyko, Attleboro; Diana McCue, Pocasset, all of Mass.

[73] Assignee: DePuy Orthopaedics, Inc., Warsaw, Ind.

[21] Appl. No.: 09/161,925

[22] Filed: Sep. 28, 1998

[51] Int. Cl.[7] .................................................. A61B 17/16
[52] U.S. Cl. .............................................................. 606/80
[58] Field of Search ................................. 606/80, 86, 82, 606/88, 89, 99, 205, 206, 207, 208

[56] References Cited

U.S. PATENT DOCUMENTS

| | | | |
|---|---|---|---|
| 4,706,660 | 11/1987 | Petersen | 128/92 VW |
| 5,129,907 | 7/1992 | Heldreth et al. | 606/80 |
| 5,284,482 | 2/1994 | Mikhail | 606/86 |
| 5,342,364 | 8/1994 | Mikhail | 606/79 |
| 5,575,793 | 11/1996 | Carls et al. | 606/80 |
| 5,658,291 | 8/1997 | Techiera | 606/86 |
| 5,716,360 | 2/1998 | Baldwin et al. | 606/80 |

OTHER PUBLICATIONS

"Surgical Technique For use with PFC® Modular Total Knee System", Universal Inset Patella, consisting of three pages including cover page unnumbered, p. 10 and p. 12.

Primary Examiner—Michael Buiz
Assistant Examiner—Anthony King
Attorney, Agent, or Firm—Nutter, McClennen & Fish, LLP

[57] ABSTRACT

A modular orthopaedic clamping tool system includes a clamp and a plurality of modular tools. The clamp has a handle having substantially parallel first and second actuation members with a jaw member integral with the first actuation member and a modular attachment element integral with the second actuation member. A linkage connects the first and second actuation members and operates to maintain a substantially parallel orientation between the actuation members while the clamp moves between open and closed positions. In addition, the orthopaedic clamping tool may be locked without causing an excessive clamping force on a clamped bone.

20 Claims, 3 Drawing Sheets

MODULAR ORTHOPAEDIC CLAMPING TOOL

CROSS-REFERENCE TO RELATED APPLICATION

Not Applicable.

STATEMENT REGARDING FEDERALLY SPONSORED RESEARCH

Not Applicable.

BACKGROUND OF THE INVENTION

In a variety of orthopaedic procedures, a surgeon must use a clamp to hold a bone in a stationary position. Often, the clamping is required so that the surgeon may steady the bone so that he may perform some cutting or other procedure on the bone, or the surgeon may clamp a cemented object to a bone so that the object remains stationary while the cement cures and the object permanently attaches to the bone. One such orthopaedic procedure requiring the use of an orthopaedic clamp is the implantation of a patellar prosthesis.

The patella, commonly known as the kneecap, is a hard bone having an articular surface of cartilage on the posterior side. The articular surface is held in place against the femoral condyles by the patella tendon where it provides leverage that is necessary to a properly functioning knee joint. If the articular surface becomes damaged by trauma or by degeneration, proper knee functioning breaks down, often accompanied by joint pain and immobility. In such situations, a patella prosthesis, sometimes referred to as a button, may be inserted to restore normal functioning to the knee.

Patella prostheses have also been used in total knee replacement surgery to insure a reproducible interaction of a patella with the femoral and tibial portions of the total knee replacement. Usually in such procedures the posterior side of the patella is prepared, sized and reamed so that a patella implant, when fixed to the patella, restores the reconstructed patella to its natural or original thickness.

In one procedure, the patella is prepared for the patellar implant as follows. A patellar holding clamp is placed on the patella with a clamp ring on the posterior side. The patella is then reamed with a patella reamer to a predetermined depth. One method of determining when the reamer has reached the appropriate depth involves placing a guide member on the patellar holding clamp and a stop member on the reamer. The reamer is then urged toward the patella, guided by the guide member and the clamp ring until the stop member abuts the guide member. Clamps useful for this purpose are disclosed, for example, in U.S. Pat. Nos. 5,129, 907; 5,284,482; and 5,575,793.

The patellar implant is then inserted, often with a bone cement, into the prepared bed. A patellar holding clamp may be used to push the patellar implant into the prepared bed, or to hold the implant in place while the bone cement cures. Clamps useful for this purpose are shown in U.S. Pat. No. 4,706,660 (clamp 110).

The prior art clamps are generally useful for their intended purposes, but many of the clamps employ a locking feature, often a threaded rod with a threaded knob, that directly squeezes either the jaws of the clamp or the handle members of the clamp and increases the compression on the bone held between the jaws. Such locking devices must be carefully employed by a surgeon in order not to over tighten the clamp. In addition, existing clamps are limited to a single type and a single size of jaw member, resulting in the need to maintain an inventory of clamps for each different orthopaedic use or size.

SUMMARY OF THE INVENTION

The present invention provides a modular orthopaedic clamping tool system. The modular orthopaedic clamping tool system includes a clamp and a plurality of modular tools. The clamp has a handle having substantially parallel first and second actuation members with a jaw member disposed on the first actuation member and a modular attachment element integral disposed on second actuation member. A linkage connects the first and second actuation members and operates to maintain a substantially parallel orientation between the actuation members while the clamp moves between open and closed positions.

In addition, the present invention provides an orthopaedic clamping tool that may be locked without causing an excessive clamping force. The orthopaedic clamping tool includes a handle having first and second actuation members and jaws integral with each actuation member. A linkage connects the actuation members and includes a first diagonal member rotatably coupled to the first actuation member and rotatably and slidably coupled to the second actuation member and a second diagonal member rotatably coupled to the second actuation member and rotatably and slidably coupled to the first actuation member. The first and second diagonal members are also rotatably coupled to each other.

In order to provide locking, the orthopaedic clamping tool may further include a rod coupled to the first diagonal member proximate to the diagonal member's coupling to the second actuation member, and a locking element. The rod extends past the end of the second actuation member and the locking element prevents relative movement between the rod and the end of the second actuation member.

Alternatively, the locking element may be coupled to the first diagonal member proximate to the diagonal member's coupling to the second actuation member. The locking element may then engage the second actuation member to prevent relative sliding movement between the first diagonal member and the second actuation member.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
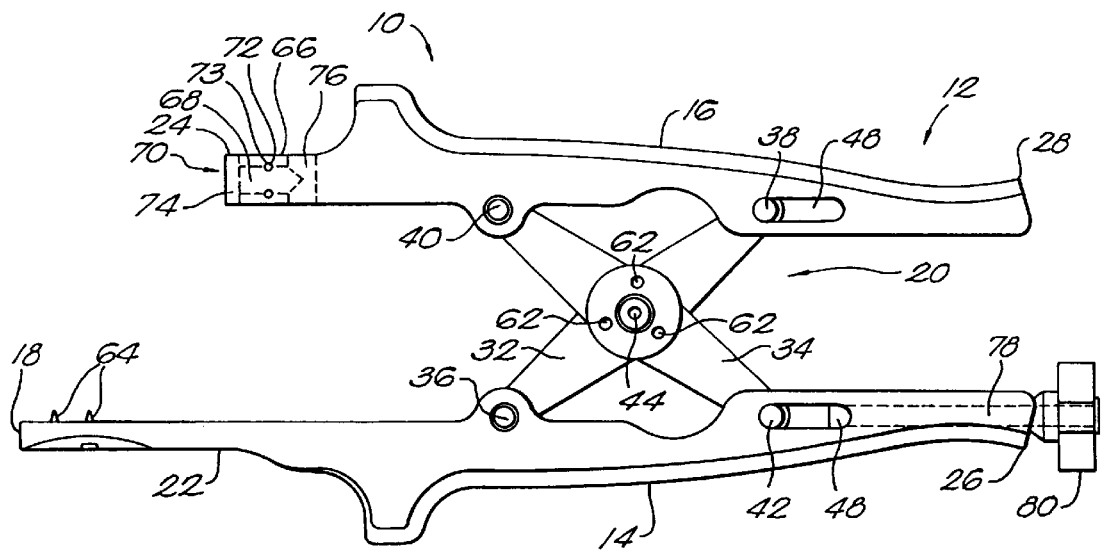
FIG. 1 is a side view of an orthopaedic clamp of the invention shown in an open position.
Figure 2:
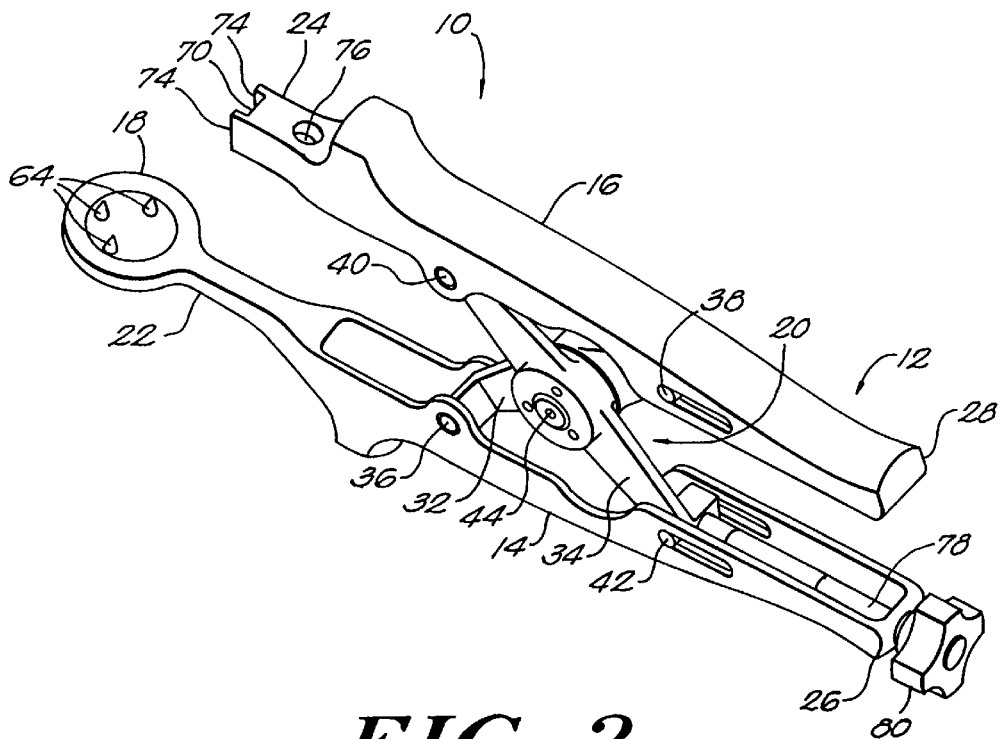
FIG. 2 is a perspective view of the locking orthopaedic clamp of FIG. 1 in an open position.

An orthopaedic clamp 10 of the invention, illustrated in FIGS. 1 and 2, includes a handle portion 12 having first and second actuation members 14, 16, a jaw member 18 integral with the first actuation member 14, and a linkage 20 connecting the actuation members. Each actuation member 14, 16 has a first, clamping end 22, 24 proximate to the jaw 18 and a second opposed end 26, 28.

Linkage 20 connects the first and second actuation members 14, 16 and includes a first diagonal member 32 and a second diagonal member 34. The first diagonal member 32 is rotatably coupled to the first actuation member 14 at a first pivot point 36. First diagonal member 32 is also rotatably and slidably coupled to the second actuation member 16 at a second, sliding pivot point 38.

Second diagonal member 34 is rotatably coupled to the second actuation member 16 at a third pivot point 40 and is rotatably and slidably coupled to the first actuation member 14 at a fourth, sliding pivot point 42. Second diagonal member 34 is also rotatably coupled to the first diagonal member 32 at a fifth pivot point 44.

Figure 3:
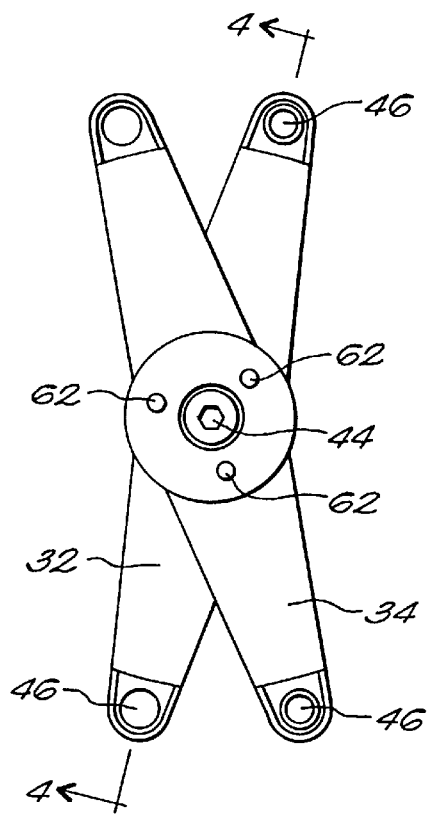
FIG. 3 is a side view of diagonal members of the clamp of FIG. 1.
Figure 4:
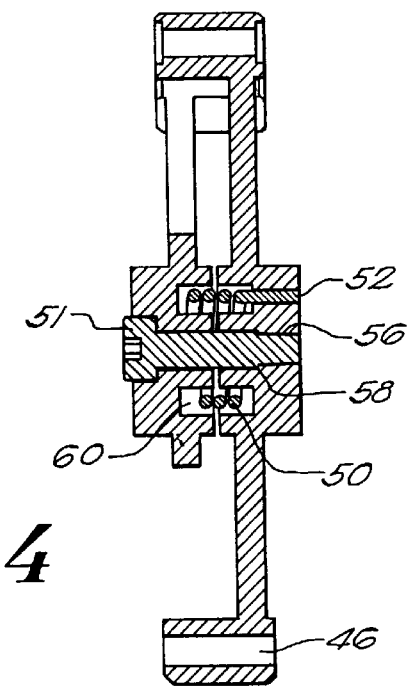
FIG. 4 is a cross sectional view of the diagonal members of FIG. 3 taken along line 4—4.

The rotatable connections may be formed at each of the first four pivot points 36, 38, 40, 42 using substantially cylindrical pivot pins (not shown) to rotatably connect the diagonal members. The first four pivot points 36, 38, 40, 42, which are integral with the actuation members 14, 16, include two separated through holes on separate walls of the generally tubular actuations members for each rotatable connection. The diagonal members are rotatably coupled to the actuation members by sliding the a diagonal member, having a through hole 46 at its connecting point (see FIGS. 3 and 4) between the separated through holes in an actuation member. A pivot pin extends through the linearly arranged holes to rotatably connect the diagonal member to the actuation member. Rotating and sliding couplings may be created at second and fourth pivot points 38, 42 by providing opposed slots 48 rather than through holes on opposed walls of the actuation member. A person of ordinary skill in the art will understand that other methods of rotatably connecting the links may be employed without departing from the spirit of the invention.

Figure 5:
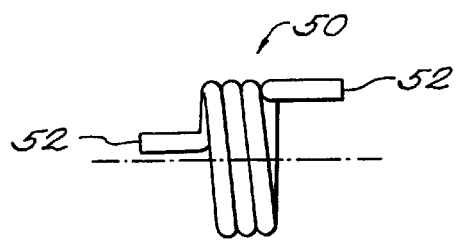
FIG. 5 is a side view of a spring used with the diagonal members of FIGS. 3 and 4.

The fifth pivot point 44 may be arranged in a similar fashion to the other pivot points, but may also include a bias element. In the embodiment shown in FIGS. 4 and 5, a torsion spring 50 is provided as the bias element and is enclosed by the diagonal members at the fifth pivot point 44. The torsion spring 50 includes a coil of resilient material with extending connecting portions 52 extending at right angles to the coiled material.

The first and second diagonal members 32, 34 may be coupled using a shoulder screw 54 having a threaded portion 56 for connecting the diagonal members and a non-threaded portion 58 for allowing rotation between the two members. Torsion spring 50 is located in a cavity 60 formed at the connection of the diagonal members 32, 34 with at least one extending portion 52 connected to each diagonal member, for example, by placing the extending portion 52 through holes 62 provided in the diagonal members in proximity to the fifth pivot point. The torsion spring 50 and configuration disclosed herein provide a smooth and steady rotational bias force to the diagonal members 32, 34 about the fifth pivot point 44. In addition, because the torsion spring 50 is enclosed within cavity 60, there is no danger that the spring will catch, bind, or fall off during use.

Jaw 18, as illustrated in FIGS. 1 and 2, is generally sized and configured to hold a patella and spikes 64 may be provided on jaw 18 to properly locate and retain a patella to the clamp 10. Of course, jaw 18 could be configured for use with other orthopaedic applications.

A modular attachment element 66 is provided integral with second actuation member 16 at its first, clamping end 24 and includes a generally cylindrical bore 68 formed in an end face 70 at the first, clamping end 24 of the second actuation member. Bore 68 includes a circumferential groove 72 that may engage a compressible ring 73 to lock a modular tool into place as a second jaw of the clamp. The modular attachment element 66 also includes raised ridges 74 on the end face 70 that may help to orient, and maintain the orientation of, a modular tool. A transverse through hole 76 communicates with bore 68 and is accessible from outside the second actuation member 16 so that a dissociation tool (not shown) may be inserted into the transverse through hole 76 to disengage a modular tool that might be associated with the modular attachment element 66. While clamp 10 is illustrated with jaw 18 formed integrally with first actuation member 14 and modular attachment element 66 formed on second actuation member 16, either or both of the first and second actuation members 14, 16 may have modular attachments.

Figure 6:
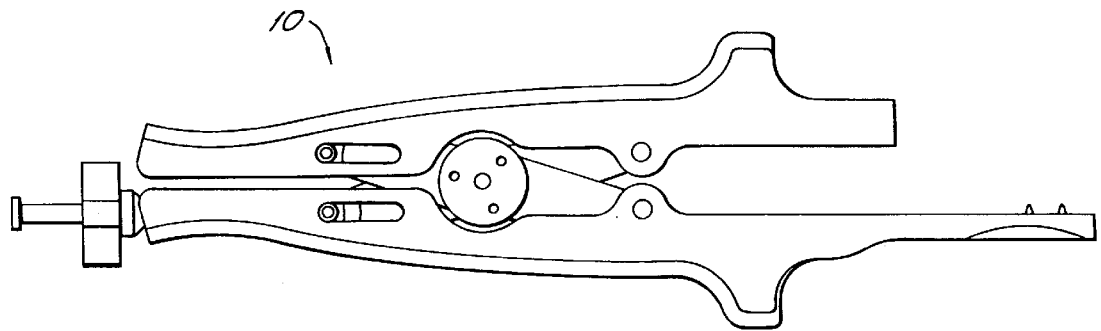
FIG. 6 is a side view of the locking orthopaedic clamp of FIG. 1 in a closed position.

Orthopaedic clamp 10 of the invention is shown in FIGS. 1 and 2 in an open position. The actuation members 14, 16 are substantially parallel to each other and jaws 18, 66 are spaced apart. As used herein, the term "jaws" refers to tool members, such as jaw 18 and modular attachment element 66 along with any modular tool that might be associated therewith, located at the first, clamping end 22, 24 of actuation members 14, 16, regardless of whether such tools are modular or are integrally formed. In operation, a surgeon grasps the clamp 10 by handle 12 and squeezes, driving the jaws closer together until a workpiece, such as a bone, or in particular a patella, is grasped between the jaws with a desired level of compression resulting in a closed position. Clamp 10 is illustrated in a closed position in FIG. 6. Preferably, linkage 20 is designed so as to maintain actuator elements 14, 16, and thus the jaws, in a substantially parallel orientation throughout the range of motion of the clamp.

Orthopaedic clamp 10 may also be provided with a locking element that operates to lock the sliding of at least one of the sliding pivot points 38, 42. The locking element may include a threaded rod 78 attached to one of the sliding pivot points 42 and a threaded knob 80 engaged with the threaded rod 78. As clamp 10 is moved from an open to a closed position, sliding pivot points 38, 42 slide toward the second ends 26, 28 of actuation members 14, 16. This movement forces rod 78 to slide in a direction past the second end 26, 28 of the actuation members 14, 16. Turning the threaded knob 80 so that it moves down rod 78 to contact the second end 26, 28 of an actuation member 14, 16 locks clamp 10 against moving towards its open position. In use, when a surgeon closes clamp 10 about a bone so that clamp 10 can move no farther toward in a closing direction, moving knob 80 to a second end 26, 28 of an actuation member 14, 16 locks clamp 10 against any movement. When a bias element, such as torsion spring 50, biases clamp 10 to its open position, clamp 10 will rest in whatever position knob 80 is set to and can only be tightened in a closing directing without resetting the knob 80.

Knob 80 provides a slight mechanical advantage in clamping a bone with clamp 10. That is, as knob 80 is tightened, there will be a slight pressure increase between the jaws of the clamp 10 holding a bone. This is because tightening knob 80 applies a slight leverage that urges the sliding pivot point to which rod 78 is attached toward the second end of its actuation member. Through mechanical action, this movement urges the jaws of clamp 10 toward each other, i.e. in a closing direction. This mechanical advantage can be useful to eliminate any slack in linkage 20 that may cause loosening of the jaws when a surgeon releases the handle 12 of clamp 10. While a slight mechanical advantage in the locking element may be beneficial, too much mechanical advantage may be detrimental. If too much mechanical advantage is supplied during locking, it is possible that a surgeon may over tighten the locking element and supply excessive clamping pressure at the jaws. While the locking mechanism of clamp 10 provides a slight mechnical advantage, that advantage is significantly less than that of known clamps such as the clamp disclosed in FIG. 1 of U.S. Pat. No. 5,575,793. Accordingly, the risk of over tightening is greatly reduced or eliminated using clamp 10.

Figure 7:
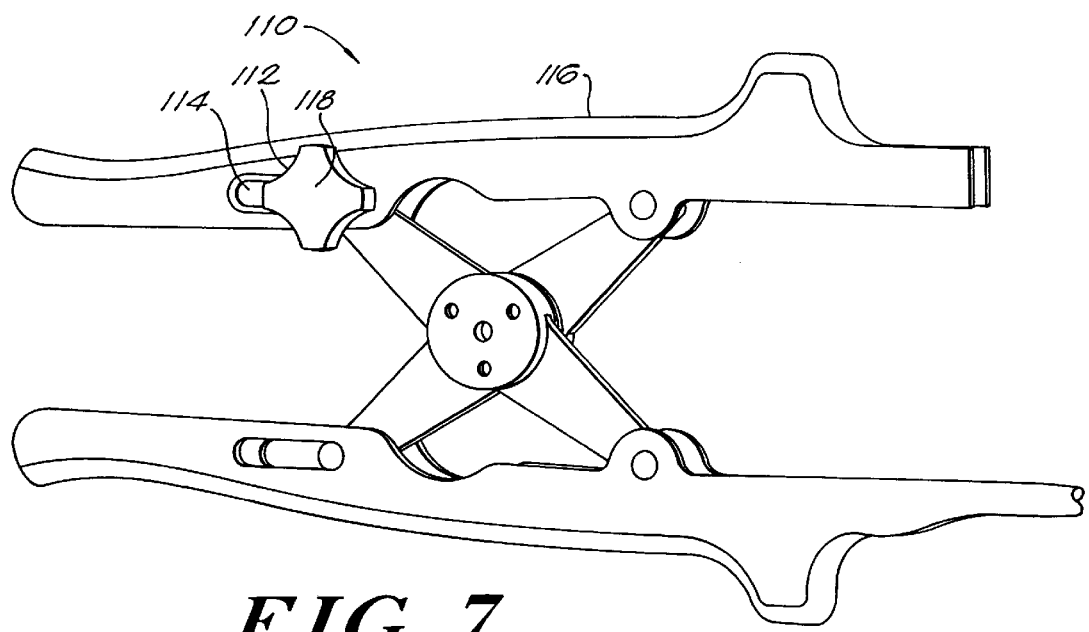
FIG. 7 is a side view of an additional orthopaedic clamp of the invention in an open position.

An additional orthopaedic clamp 110 of the invention having a locking element that provides no mechanical advantage is illustrated in FIG. 7. Clamp 110 also has a threaded rod (not shown), but the rod extends outward from sliding pivot point 112 through slot 114 in actuation member 116. A threaded knob 118 is provided on the rod and tightens to the surface of actuation member 116 to prevent sliding pivot point 112 from sliding in either direction. This action locks clamp 10 in position without providing any mechanical advantage to the jaws.

Figure 8:
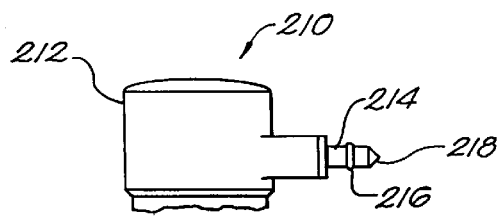
FIG. 8 is a side view of a modular tool of the invention.

A modular tool 210 useful for guiding a patella reaming instrument is illustrated in FIG. 8. Modular tool 210 has a guide body 212 and a mating element 214. The mating element 214 is generally cylindrical and is configured to mate with modular attachment element 66. Mating element 214 includes a locking feature 216 suitable to engage locking ring 73 and an angled end 218. The precise shape of the mating element and corresponding modular attachment element, as well as the choice of whether the male element is located on the modular tool or on the clamp, may be selected by a person of ordinary skill in the art in keeping with the spirit of the invention.

Modular tool 210 may be selected from a group or kit of modular tools that may be used with orthopaedic clamp 10. The kit may include reamer guides such as modular tool 210 of different sizes or capable of guiding a reamer to different areas of a clamped bone. The kit may also include a modular jaw element configured to hold a patella implant in place to a patella to allow for holding cement to cure, or a modular jaw element configured as a drill guide to drill holes in a patella to receive pegs.

It will be understood that the foregoing is only illustrative of the principles of the invention, and that various modifications can be made by those skilled in the art without departing from the scope and spirit of the invention.

All references cited herein are expressly incorporated by reference in their entirety.

What is claimed is:

1. A modular orthopaedic clamping tool system having an open position and a closed position for clamping a bone comprising:
   (a) a clamp including:
      a handle comprising substantially parallel first and second actuation members;
      a jaw member provided on the first actuation member;
      a first modular attachment means provided on the second actuation member for releasably attaching a modular tool; and
      a linkage connecting the first and second actuation members, the linkage operating to maintain a substantially parallel orientation between the actuation members while the clamp moves between the opened and closed positions; and
   (b) a plurality of modular tools, each having a second modular attachment means for releasably mating with the first modular attachment means.

2. The system of claim 1, wherein the jaw is sized to hold a patella.

3. The system of claim 2, wherein the plurality of tools includes at least one patella resection guide.

4. The system of claim 3, wherein the plurality of tools includes a plurality of patella resection guides.

5. The system of claim 2, wherein the plurality of tools includes at least one patella implant holder.

6. The system of claim 1, wherein the linkage includes a first diagonal member and a second diagonal member.

7. The system of claim 6, wherein the first diagonal member is rotatably coupled to the first actuation member and rotatably and slidably coupled to the second actuation member and the second diagonal member is rotatably coupled to the second actuation member and rotatably and slidably coupled to the first actuation member, the first and second diagonal members being rotatably coupled to each other.

8. The system of claim 1, wherein a first one of the first and second modular attachment means comprises a wall defining a generally cylindrical bore, and a second one of the first and second modular attachment means comprises a male attachment element sized to mate within the generally cylindrical bore.

9. The system of claim 2, wherein a first one of the generally cylindrical bore and the male mating element includes a circumferential groove and a second one of the generally cylindrical bore and the male mating element includes a compressible retaining ring sized to releasably attach a modular tool to the clamp.

10. The system of claim 2, wherein the system includes an externally accessible through hole intersecting the generally cylindrical bore, and the male attachment element has an angled end so that insertion of a release tool into the through hole contacts the angled end of a mated tool to push the tool out of its mating engagement with the bore.

11. An orthopaedic clamping tool having an open position and a closed position for clamping a bone comprising:
   a handle comprising first and second elongate actuation members;
   a first jaw member disposed at a first end of the first actuation member;
   a second jaw member disposed at a first end of the second actuation member; and
   a linkage connecting the first and second actuation members comprising:
      a first diagonal member rotatably coupled to the first actuation member and rotatably and slidably coupled to the second actuation member; and
      a second diagonal member rotatably coupled to the second actuation member and rotatably and slidably coupled to the first actuation member;
      the first and second diagonal members being rotatably coupled to each other; and
      a locking means for locking the sliding of the second diagonal member with respect to the first actuation member without resulting in an excessive clamping force.

12. The tool of claim 11, wherein the locking means comprises a locking element coupled to the second diagonal member proximate to the diagonal member's coupling to the first actuation member and to the first actuation member to prevent relative sliding movement between the second diagonal member and the first actuation member.

13. The tool of claim 12, wherein the locking element comprises a rod coupled to the second diagonal member proximate to the diagonal member's coupling to the first actuation member, the rod extending past a second end, opposite the first end, of the first actuation member, and a stop element for preventing relative movement between the rod and second end of the actuation member.

14. The tool of claim 12, wherein at least one of the jaw members is a modular tool element.

15. The tool of claim 14, wherein the modular tool element is selected from a group of modular tools.

16. The tool of claim 14, wherein the modular tool element is a patella reaming guide.

17. The tool of claim 14, wherein the modular tool element is a patella implant holder.

18. An orthopaedic clamping tool having an open position and a closed position for clamping a bone comprising:
- a handle comprising first and second elongate actuation members;
- a first jaw member disposed at a first end of the first actuation member;
- a second jaw member disposed at a first end of the second actuation member; and
- a linkage connecting the first and second actuation members comprising:
  - a first diagonal member rotatable coupled to the first actuation member and rotatably and slidably coupled to the second actuation member; and
  - a second diagonal member rotatably coupled to the second actuation member and rotatably and slidably coupled to the first actuation member;
  - the first and second diagonal members being rotatably coupled to each other; and
  - a bias element coupled to each diagonal member to bias the clamping tool to the open position wherein the sliding of the second diagonal member with respect to the first actuation member locks without resulting in an excessive clamping force.

19. The tool of claim 13, further comprising a rod coupled to the first diagonal member proximate to the diagonal member's coupling to the second actuation member, the rod extending past a second end, opposite the first end, of the second actuation member, and a locking element for preventing relative movement between the rod and the second end of the second actuation member in the direction of the bias.

20. The tool of claim 13, wherein the bias element comprising a torsion spring having a coiled portion and a first extension portion engaged with the first diagonal member and a second extension portion engaged with the second diagonal member.

* * * * *